United States Patent
Ragnarson et al.

(10) Patent No.: US 7,598,427 B2
(45) Date of Patent: Oct. 6, 2009

(54) ABSORBENT ARTICLE WITH IMPROVED LEAKAGE PROTECTION

(75) Inventors: Christina Ragnarson, Göteborg (SE); Kent Hermansson, S- Västra Frölunda (SE); Åsa Lindström, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 1371 days.

(21) Appl. No.: 10/203,289

(22) PCT Filed: Feb. 19, 2001

(86) PCT No.: PCT/SE01/00359

§ 371 (c)(1),
(2), (4) Date: Dec. 4, 2002

(87) PCT Pub. No.: WO01/66058

PCT Pub. Date: Sep. 13, 2001

(65) Prior Publication Data

US 2003/0139724 A1    Jul. 24, 2003

(30) Foreign Application Priority Data

Mar. 6, 2000 (SE) .................................. 0000729

(51) Int. Cl.
*A61F 13/20* (2006.01)
(52) U.S. Cl. ..................................... 604/378
(58) Field of Classification Search ................. 604/378
See application file for complete search history.

(56) References Cited

U.S. PATENT DOCUMENTS 5,817,079 A  10/1998  Bergquist et al.

FOREIGN PATENT DOCUMENTS

| EP | 1057463 A2 * | 12/2000 |
|----|----|----|
| JP | 08-010287 | 1/1996 |
| JP | 10-043238 | 2/1998 |
| WO | 95/10993 | 4/1995 |
| WO | 98/33463 | 8/1998 |
| WO | 99/16398 | 4/1999 |

* cited by examiner

*Primary Examiner*—Tatyana Zalukaeva
*Assistant Examiner*—Ginger T Chapman
(74) *Attorney, Agent, or Firm*—Buchanan Ingersoll & Rooney PC

(57) ABSTRACT

The invention relates to an absorbent article for taking up body fluids, with a longitudinal direction, a transverse direction, a crotch portion (8) and two end portions (6, 7), and having side edges (9, 10) extending in the longitudinal direction and end edges (11, 12) extending in the transverse direction, and comprising a liquid-permeable cover sheet (2) and a liquid-tight cover sheet (3), and an absorbent body (4) arranged between the cover sheets (2, 3), and further comprising barriers which are arranged along the side edges (9, 10) of the article and which are raised up from the liquid-permeable cover sheet (2). The liquid-permeable cover sheet (2) has a central zone (30) which is arranged essentially in the crotch portion (8) of the article, and two end zones (31, 32) which are arranged at the end portions (6, 7) of the article, the liquid-permeable cover sheet (2) being more hydrophilic in the central zone (30) than in the end zones (31, 32).

9 Claims, 4 Drawing Sheets

ABSORBENT ARTICLE WITH IMPROVED LEAKAGE PROTECTION

TECHNICAL FIELD

The invention relates to an absorbent article for taking up body fluids, with a longitudinal direction, a transverse direction, a crotch portion and two end portions, and having side edges extending in the longitudinal direction and end edges extending in the transverse direction, and comprising a liquid-permeable cover sheet and a liquid-tight cover sheet, and an absorbent body arranged between the cover sheets, and further comprising edge barriers which are arranged along the side edges of the article and which are raised up from the liquid-permeable cover sheet.

BACKGROUND

Absorbent articles intended for taking up body fluids are constant targets for improvement, particularly with respect to leakage protection. A problem particularly associated with absorbent articles intended for incontinent adults is that of leakage due to the fact that large amounts of liquid are eliminated during a short period of time. In this connection, it may happen that not all the liquid has time to penetrate into the absorbent article, and instead some of the liquid flows out across the surface of the article and gives rise to leakage. In the context of diapers too, leakage can occur on account of the fact that a large amount of liquid impacts the article in a short time. A particular concern in connection with diapers for infants is the leakage of excrement. Since infants often have very free-flowing stools, these occur as a liquid and can easily run out over the edge of the diaper. Such leakage of excrement is particularly unpleasant, and the stains which occur on the soiled clothes and bedlinen are very difficult to wash off.

A liquid-absorbing article such as a diaper or incontinence protector is usually provided with elastic members. These elastic members have two main functions. On the one hand, they are used to shape the absorbent article in order to maintain a good fit of the article to the shape of the user's body, and, on the other hand, they are used to create different types of leakage protectors. For example, most diapers are provided with elastic members along the side edges, as a result of which elastic, sealing and leakage-tight leg bands are obtained once the diaper is placed on the user's body. It is also possible to create liquid-collecting depressions, pockets and raised barriers by arranging elastic members on an absorbent article.

It has also been proposed to provide absorbent articles with other types of barriers which are raised from the surface of the article and which prevent uncontrolled flow of liquid across the surface. Examples of non-elastic barriers are material folds and corrugations, built-up banks or the like. In addition to guiding and controlling the flow of liquid on the surface of an absorbent article, such raised leakage barriers can also be arranged along the side edges of the article in order to prevent liquid from leaking out of the article.

Patent Specification SE-C2 502 818 describes a liquid-absorbing article intended for single use, such as a diaper, a sanitary towel or the like. The article described has an essentially elongate shape and comprises an absorbent body and a cover enclosing the absorbent body, with a liquid-permeable inner sheet and an outer sheet. The article further comprises contracting elastic members connected to at least one sheet.

A further problem which arises when using absorbent articles is that the body fluids taken up by the article come into contact with the user's skin and can thus give rise to skin irritation. If the absorbent article contains excrement, it may also be desirable to keep the excrement at a distance from the user's body, since this considerably facilitates cleaning of the user's pubic area when the article is to be changed.

Patent Specification WO 95/10993 discloses a disposable diaper with improved ability to keep bodily excretions away from the user's skin, which diaper comprises a sheet which protects the underwear, a liquid-permeable surface material, an absorbent element placed between the protective sheet and the surface material, and a liquid-tight nonwoven covering which has an opening in the crotch area, and with edge portions around the opening in the liquid-tight nonwoven covering forming sealing flaps around the opening.

For the diaper to be able to absorb bodily excretions more quickly and to be able to retain these in a more effective manner, WO 95/10993 proposes that the absorbent element has an absorbent sheet on which a spreading sheet is arranged and that the dimensions of the opening in the nonwoven covering are smaller in the longitudinal and transverse directions than the corresponding dimensions of the spreading sheet. The disposable diaper described in WO 95/10993 is said to comprise elastic means at the edges of the opening in the nonwoven covering and along the longitudinal outer edges of the diaper.

However, despite all efforts to prevent leakage when using absorbent articles, it still happens that liquid leaks out from the articles, principally at their end edges. Thus, there is still a great need for further improved leakage protection.

SUMMARY

It is an object to make available a liquid-absorbing article for disposable use in which the risk of leakage past the end edges has been substantially reduced.

An article designed according to the embodiments of the invention and of the type set out by way of introduction is distinguished primarily by the fact that the liquid-permeable cover sheet has a central zone which is arranged essentially in the crotch portion of the article, and two end zones which are arranged at the end portions of the article, the liquid-permeable cover sheet being more hydrophilic in the central zone than in the end zones.

According to one embodiment of the invention, raised edge barriers are arranged along at least one end edge of the article.

The raised edge barriers can, for example, be formed by material folds in the liquid-permeable cover sheet, or they can be formed by separate material pieces which have been applied on the liquid-permeable cover sheet. The edge barriers can comprise absorbent material such as absorbent fibre material, superabsorbent material, absorbent or nonabsorbent foam material, fibre wads, or the like. The raised edge barriers can further comprise elastic members which help to raise the barriers from the liquid-permeable cover sheet and which also affect the shaping of the absorbent article. The elastic members can in this case be present in the form of elastic bands or filaments which, for example, have been arranged inside material folds or have been secured to the barriers, for example, by adhesive bonding or welding. It is also possible to form edge barriers made entirely of elastic material, for example bands of elastic foam material, or nonwovens.

To achieve a good barrier effect, it is preferable for the raised edge barriers to comprise material which withstands liquid penetration. Such material can be a hydrophobic nonwoven fabric, plastic film, or a coating of plastic, wax or the like.

The raised edge barriers can be made from one and the same material layer which is arranged across that surface of the liquid-permeable cover sheet which, during use, is intended to be directed towards the user. Such a barrier sheet is in this case provided with an opening through which liquid can pass into the article. Around the opening, the barrier sheet extends contiguously along the side edges and end edges of the article, as a result of which a pocket-like space is formed between the edge barriers and the liquid-permeable cover sheet.

To achieve a difference in hydrophilicity between the central zone and the end zones of the liquid-permeable surface material, the liquid-permeable surface material can have different material compositions in the central zone and the end zones. For example, the liquid-permeable surface material can consist of a fibre material in which the central zone comprises a greater proportion of hydrophilic fibres than do the end zones.

Another way of achieving the difference in hydrophilicity between the central zone and the end zones of the liquid-permeable surface material is by the fact that the liquid-permeable surface material consists of an essentially hydrophobic material which has been treated to obtain hydrophilicity in the central zone. For example, the central zone can be treated with surfactants or other wetting agents.

The hydrophilic central zone of the liquid-permeable surface material can be centrally arranged in the longitudinal direction of the article. Alternatively, the central zone of the liquid-permeable surface material can be arranged slightly offset towards one end portion of the article. The hydrophilic central zone can extend out to the side edges of the article or end slightly inside of these.

It has been found to be preferable for the central zone of the liquid-permeable surface material to have an extent in the longitudinal direction of the article corresponding to 25-75% of the length of the article, and an extent in the transverse direction of the article corresponding to 60-100% of the width of the article.

An absorbent article according to the embodiments of the invention is moreover advantageously provided with at least one elastic member, which is prestressed and in direct contact with the absorbent body, and extends in an arcuate curve across the absorbent body, between the side edges of the article.

By combining raised edge barriers with a liquid-permeable cover sheet which has a central zone with greater hydrophilicity than in the end zones on both sides of the central zone, it has been found to be possible to achieve very high leakage protection. The leakage protection afforded by an article according to embodiments of the invention is thus greater than would have been expected on the basis of the leakage protection afforded by an article with only raised edge barriers, or with only a hydrophilic central zone.

An article without raised edge barriers and with a liquid-permeable sheet which has a central, hydrophilic zone and surrounding zones which are more hydrophobic affords considerably less leakage protection than a corresponding article with a surface layer without hydrophobic end zones. It is therefore particularly surprising that it is possible to improve the leakage protection of an article with raised edge barriers by using a liquid-permeable surface sheet with zones of different hydrophilicity/hydrophobicity.

BRIEF DESCRIPTION OF THE FIGURES

The invention will be described in greater detail below with reference to the illustrative embodiments which are shown in the attached drawings, in which.

DESCRIPTION OF ILLUSTRATIVE EMBODIMENTS

Figure 1:
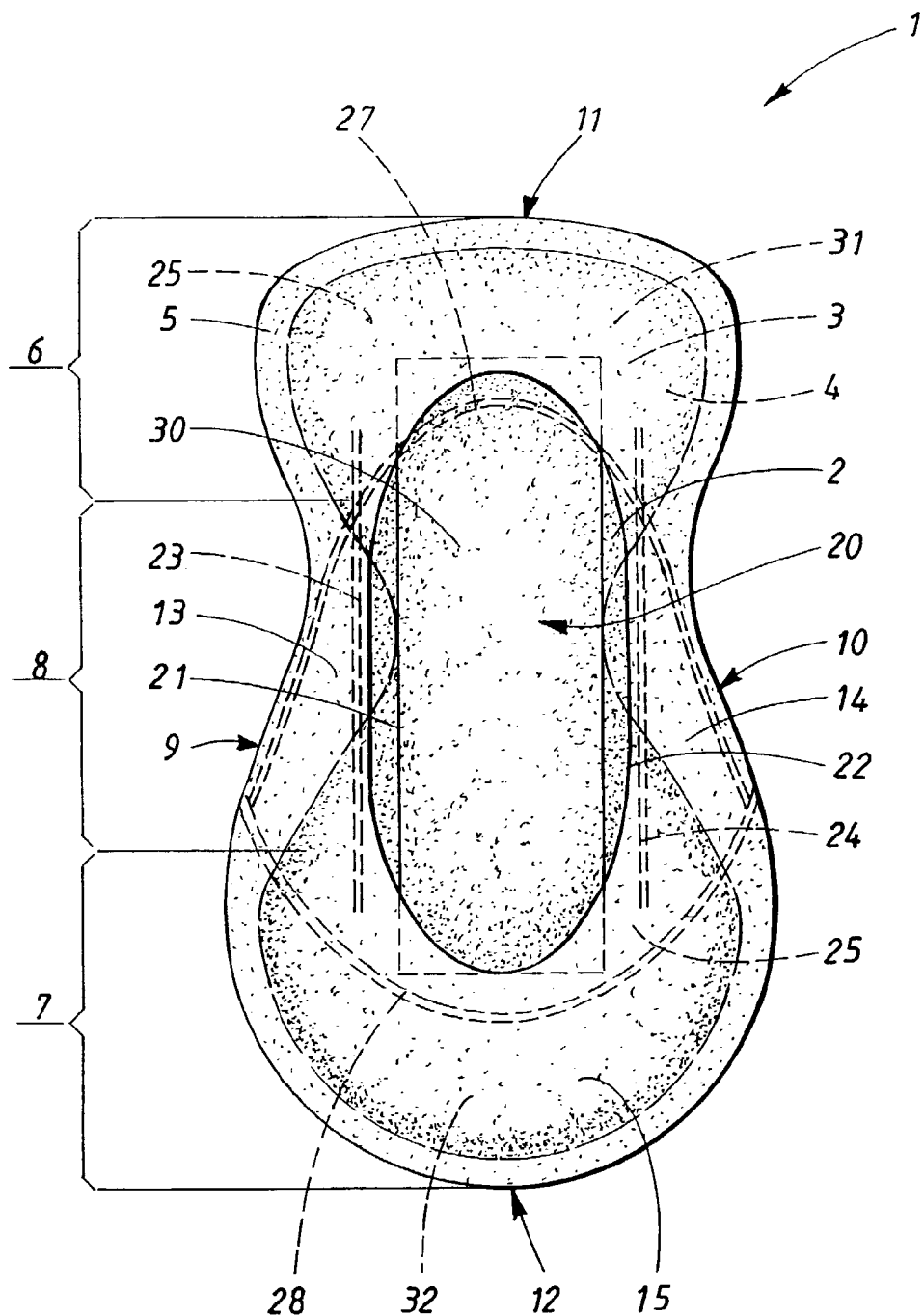
FIG. 1 shows a plan view of an incontinence protector according to a first embodiment of the invention.

The incontinence protector 1 shown in FIG. 1 comprises a liquid-permeable cover sheet 2, arranged on that side of the incontinence protector 1 which during use is intended to be directed towards the user, a liquid-tight cover sheet 3, arranged on that side of the incontinence protector 1 which during use is intended to be directed away from the user, and an absorbent body 4 enclosed between the two cover sheets 2, 3.

The material of the liquid-permeable cover sheet 2 can be, for example, a perforated plastic film, a netting of plastic or textile material, a nonwoven material, or a laminate of two or more such material layers. The plastic materials which are used in the liquid-permeable surface material are generally thermoplastics such as polyethylene or polypropylene. Suitable nonwoven materials can comprise natural fibres, such as cellulose or cotton, or synthetic fibres, such as polyethylene, polypropylelne, polyester, polyurethane, nylon or regenerated cellulose. It is also possible to use nonwoven material made from fibres with two or more components, and mixtures of different types of fibres.

The liquid-permeable cover sheet 2 will admit liquid and convey it towards the absorbent body 4. Moreover, the cover sheet 2 should be able to prevent so-called re-wetting, that is to say when absorbed body fluid passes back out of the absorbent body 4, and it should be soft and comfortable against the user's body.

The liquid-tight cover sheet 3 is made of a liquid-impermeable material. Thin, liquid-tight plastic films are suitable for this purpose. However, it is also possible to use material which is liquid-permeable to begin with, but which has been provided with a coating of plastic, resin or other liquid-tight material. In this way, leakage of liquid from the underside of the absorbent article is prevented. The liquid-tight cover sheet 3 can thus consist of any material which is compatible with the skin and satisfies the criterion of liquid impermeability. Examples of materials which are suitable as liquid barrier layer are plastic films, nonwoven materials, and various types of laminates. Plastic films that can be used are, for example, those consisting of polyethylene, polypropylene or polyester. Alternatively, the liquid-tight cover sheet 3 can consist of a laminate of a liquid-impermeable plastic sheet, directed towards the absorbent body, and a nonwoven layer directed towards the user's underwear. Such a construction provides a leakage-proof barrier layer with a textile feel.

The absorbent body 4 can advantageously be made up of cellulose fluff pulp. This can be provided in the form of rolls, bales or sheets which are dry-defibred and converted in fluffed form to a pulp web, with or without admixture of so-called superabsorbents which are polymers having the ability to absorb several times their own weight of water or body fluid. Examples of other materials that can be used are various types of natural fibres, such as cotton fibres, peat or the like. It is of course also possible to use absorbent synthetic fibres or mixtures of natural fibres and synthetic fibres. The absorption material can also contain further components, such as liquid-spreading members, or binders, for example thermoplastic fibres which have been heat-treated to bind short fibres and particles together in a coherent unit. It is also possible to use various types of absorbent foam materials in the absorbent body 4. The absorbent body 4 can consist of a continuous sheet or can be made up of a plurality of different sheets or parts. The absorbent body 4 can also be profiled, i.e. it can be made with different thicknesses in different parts of the incontinence protector.

The two cover sheets 2, 3 are connected to each other outside the absorbent body 4 and form a projecting edge 5 around the entire periphery of the incontinence protector 1. The cover sheets 2, 3 can be joined together in any suitable way, for example by means of adhesive bonding, sewing, or welding with heat or ultrasound.

The incontinence protector 1 is slightly asymmetrical, but essentially hourglass-shaped, and it has a front portion 6, which during use is intended to be facing forwards on the user, and a rear portion 7, which during use is intended to be facing rearwards on the user, and an intermediate narrower crotch portion 8 intended to be arranged at the user's crotch. The incontinence protector 1 additionally has two inwardly curved side edges 9, 10, and two outwardly curved end edges 11, 12. The absorbent body 4 has approximately the same shape as the incontinence protector as a whole, but it has a slightly lesser extent in the plane. In particular, the absorbent body 4 is narrower than the two cover sheets 2, 3 at the crotch portion 8, as a result of which the cover sheets 2, 3 form flexible side flaps 13, 14 on both sides of the absorbent body 4 in the crotch portion 8.

The division of the incontinence protector 1 into two end portions 6, 7 and a crotch portion 8 must not be understood as meaning that there are sharp boundaries between the various portions 6-8, but is mainly intended to facilitate the description of the incontinence protector 1, with the starting point of the differences which exist between the various portions 6-8 as a function of how they are intended to be placed in relation to the user's body. Thus, the transition between the various portions 6-8 does not take place at defined transverse lines, but instead within diffuse transitional areas. The crotch portion 8 here constitutes that part of the incontinence protector which during use is intended to admit and absorb most of the eliminated body fluid.

A barrier sheet 15 is arranged outside the liquid-permeable cover sheet 2, on that side of the article which is intended to bear against the user's body. The barrier sheet 15 has the same extent and shape in its plane as the liquid-permeable cover sheet 2 and is fixed to the latter, by adhesive bonding, welding or the like, inside the projecting edge 5.

The barrier sheet 15 is preferably made of a thin, easily flexible and skin-compatible material. Thus, the materials and material laminates mentioned in conjunction with the two cover sheets can be used. The barrier sheet 15 advantageously has a certain ability to withstand liquid penetration, as a result of which liquid which has collected inside of the sheet 15, between this and the liquid-permeable cover sheet 2, is prevented from passing out through the sheet. However, it is advantageous for the barrier sheet 15 to be able to breathe and allow vapour and gases to pass through.

To achieve liquid resistance and increased leakage protection, the barrier sheet 15 can be treated with means imparting hydrophobicity. Examples of means imparting hydrophobicity which can be used are thin coatings of plastic, wax or the like. Alternatively, the barrier sheet can comprise a layer of hydrophobic nonwoven material, or plastic film.

The barrier sheet 15 can alternatively comprise a three-dimensional perforated film which only allows liquid through in one direction. It is thereby possible to obtain a barrier sheet 15 which is able to admit liquid which impacts the barrier sheet 15, without the liquid thereafter being able to pass out again through the sheet 15.

The barrier sheet 15 is provided with a through-opening 20 via which liquid can pass into the incontinence protector 1. Running along the longitudinal edges 21, 22 of the opening there are elastic members 23, 24 which are intended to contract the edges 21, 22 of the opening 20, so that these edges are raised from the liquid-permeable cover sheet 2 and a continuous raised barrier 25 is formed along the side edges 9, 10 of the incontinence protector and also along its end edges 11, 12. By virtue of the fact that the barrier sheet 15 is fixed along the edges 9-12 of the incontinence protector 1, a pocket-like space is formed between the liquid-permeable cover sheet 2 and the barrier sheet 15.

The elastic members 23, 24 also serve to create a flexible seal between the barrier sheet 15 and the user's body. The contraction of the material around the opening 20 is achieved by means of the elastic members 23, 24 being prestressed. Prestressing can be obtained by means of the elastic members 23, 24 being stretched out and secured to the barrier sheet 15 in the stretched-out state. Alternatively, the elastic members 23, 24 can consist of a material whose elastic contraction is activated after application to the barrier sheet 15. Such activation can be achieved, for example, by heating or by infrared radiation.

Elastic members 27, 28 are moreover arranged in connection with the absorbent body 4. A first elastic member 27 is arranged across the front portion 6 of the incontinence protector, between the liquid-permeable cover sheet 2 and the absorbent body 4. The first elastic member 27 extends in an arc directed towards the front edge 11, between the side edges 9, 10 of the incontinence protector. Correspondingly, a second elastic member 28 is arranged across the rear portion 7, in an arc towards the rear edge 12. The second elastic member 28 extends between the absorbent body 4 and the liquid-permeable cover sheet 2 and onwards into the side flaps 13, 14 which are formed by the projecting cover edge 5 on both sides of the absorbent body 4 in the crotch portion 8. Those parts of the second elastic member 28 which are arranged in the side flaps 13, 14 thus form the leg elastic of the incontinence protector.

The elastic members 27, 28 are arranged in direct connection to the absorbent body 4 in such a way that contraction of the elastic members 27, 28 also causes contraction and shaping of the absorbent body 4.

In the example shown, which is a preferred embodiment, the elastic members 27, 28 are connected to the liquid-permeable sheet 2, on the inside thereof, i.e. between the absorbent body 4 and the cover sheet 2, but they can of course alternatively be arranged on the outside of the sheet 2 or between the liquid-tight cover sheet 3 and the absorbent body 4.

The elastic members 23, 24, 27, 28 can be for example, of one or more bands of elastic material such as rubber, polyurethane, elastic nonwoven, or the like. The elastic members can be provided with a spun-round sheath which makes it easier to connect the elastic members by means of binder to components in the incontinence protector. In addition, such a sheath permits elastic movements in the elastic core. The elastic members 23, 24, 27, 28 tend to contract, and the elastic filaments or bands are for this purpose arranged with a certain amount of prestressing, as has already been described in connection with the elastic members 23, 24 which are arranged on the barrier sheet 15. Anchoring is achieved, for example, by means of adhesive binder which is applied on certain sections of the length of the elastic or along its entire length. The elastic members 27, 28 are preferably anchored both to the liquid-permeable cover sheet 2 and to the absorbent body 4.

According to an alternative embodiment, the elastic members 23, 24 fixed to the barrier sheet 15 can be omitted. In this case, a completely or partially elastic barrier sheet can be used instead. It is also possible to arrange a continuous elastic member around the whole opening 20.

According to an embodiment of the invention, the liquid-permeable cover sheet 2 has a central zone 30 and two end zones 31, 32 which are situated at the end portions 6, 7 of the incontinence protector 1. Within the central zone 30, which is situated in that area of the incontinence protector which is intended to admit most of the body fluid excreted to the incontinence protector, the liquid-permeable cover sheet 2 has a greater hydrophilicity than parts surrounding the liquid-permeable cover sheet 2. Thus, both the end zones 31, 32 are more hydrophobic than the central zone 30.

As can best be seen from FIG. 1, the central zone 30 can be a rectangular area with a width corresponding to the minimum width of the absorbent body in the crotch area 8. In the longitudinal direction of the incontinence protector, the central zone 30 extends a distance into each end portion 6, 7, where the central zone is surrounded by the more hydrophobic end zones 31, 32.

Figure 2:
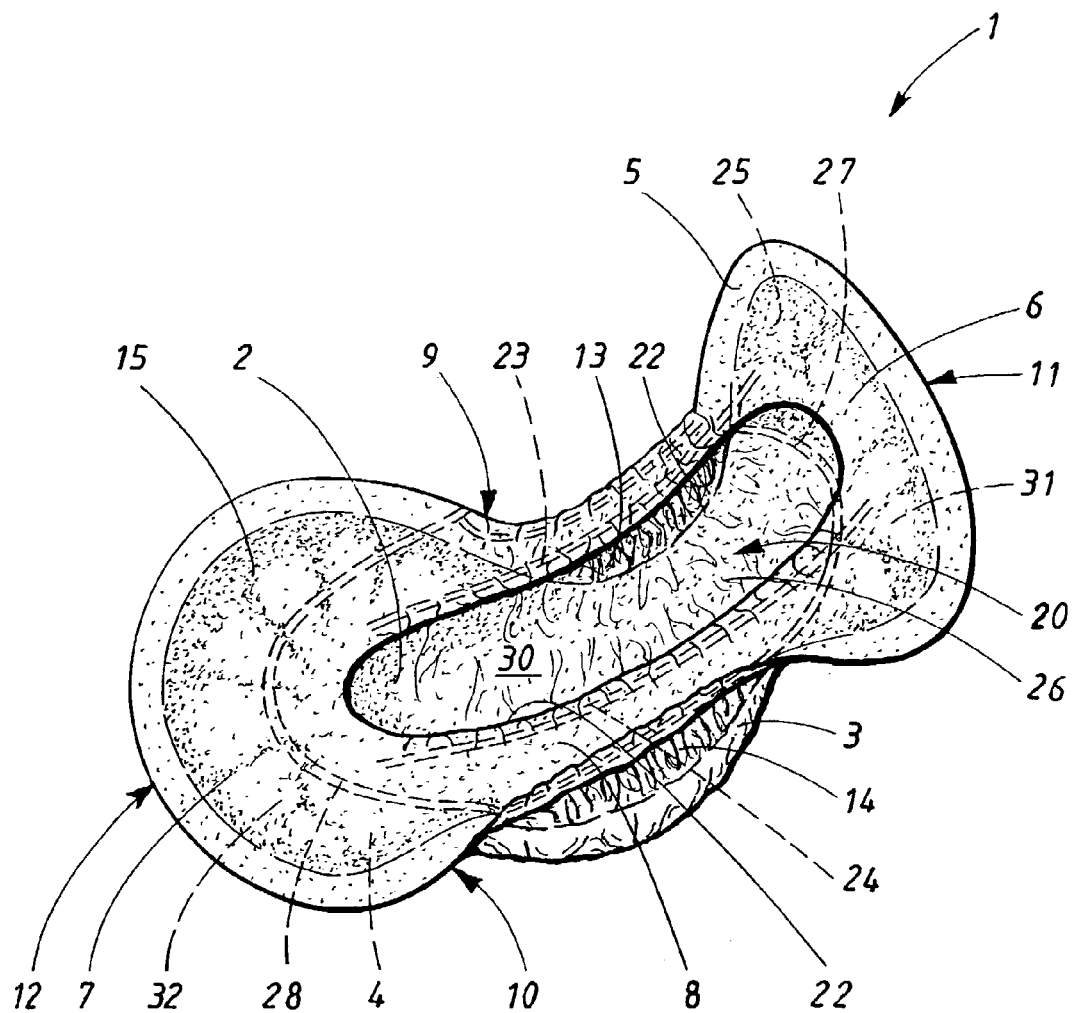
FIG. 2 shows a perspective view of the incontinence protector in FIG. 1, as it appears when the elastic members have been allowed to contract.
Figure 3:
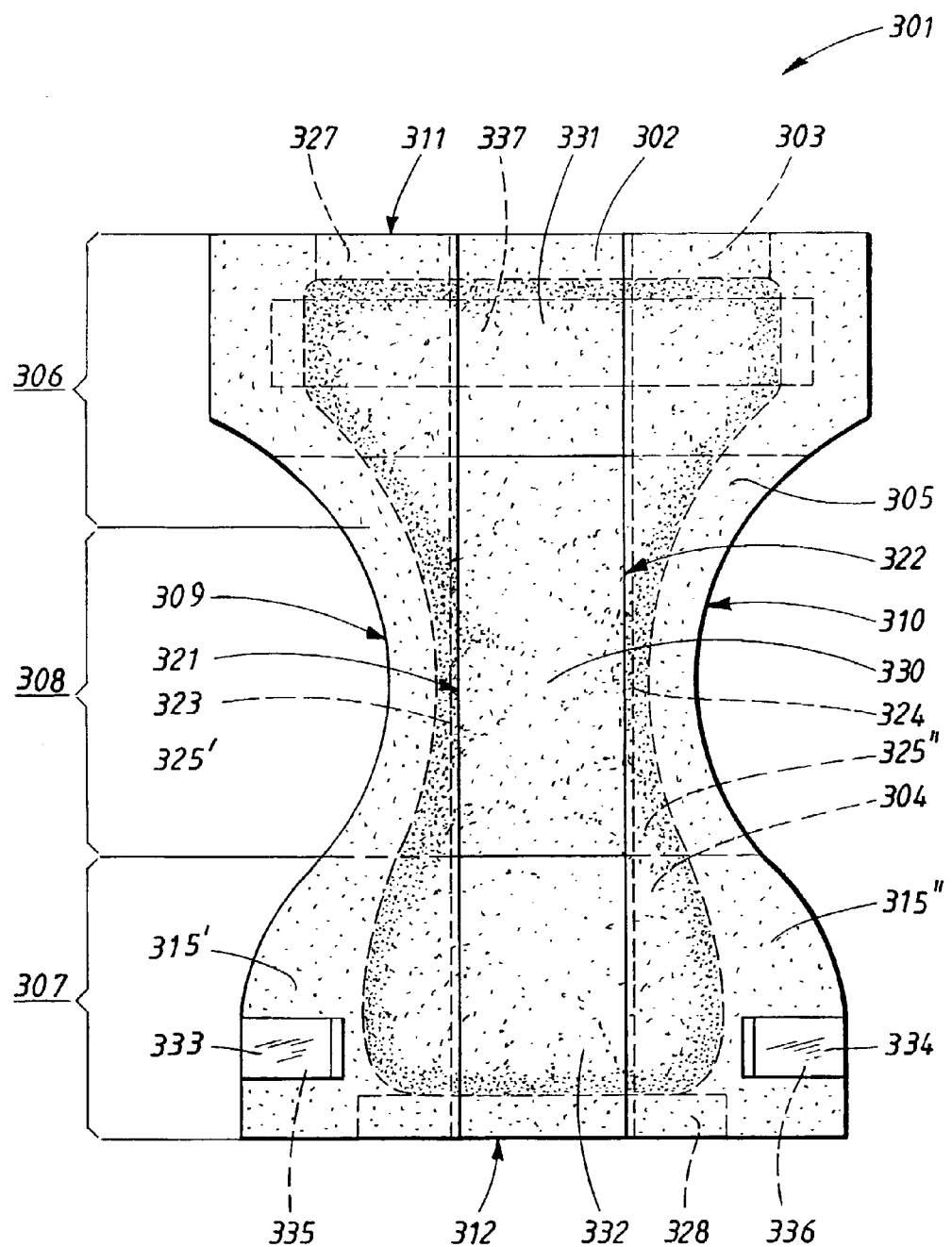
FIG. 3 shows a plan view of a diaper according to a second embodiment of the invention.

The diaper 301 shown in FIG. 3 has in part a different structure than the incontinence protector shown in FIGS. 1 and 2. However, the diaper 301 in FIG. 3 also comprises a liquid-permeable cover sheet 302 and a liquid-tight cover sheet 303 which are connected to each other at an edge 305 around an absorbent body 304 enclosed between the cover sheets 302, 303.

Like the incontinence protector in FIGS. 1 and 2, the diaper 301 in FIG. 3 can be divided into a crotch portion 308, a front end portion 306 and a rear end portion 307. The diaper also has two longitudinal side edges 309, 310 and two transverse end edges 311, 312.

The diaper 301 also has a two-part barrier sheet 315', 315" which is provided with longitudinal elastic members 323, 324. The two parts 315', 315" of the barrier sheet extend along the side edges 309, 310 of the diaper, the entire length of the diaper, and are fixed to the liquid-permeable cover sheet 302 by adhesive bonding, welding or the like within the projecting edge 5 along the side edges 309, 310 and the end edges 311, 312.

The elastic members 323, 324 are fixed in the prestressed state along the free edges 321, 322 on the barrier sheet 315', 315". This means that when the elastic members 323, 324 are allowed to contract, they also contract the free edges 321, 322 of the barrier sheets 315', 315", whereupon the rest of the diaper is curved in a direction away from the barrier sheet 315', 315" so that the parts of the barrier sheet form raised edge barriers 325', 325" along the side edges 309, 310 of the diaper. As has already been described in connection with FIGS. 1 and 2, the material in the barrier sheet 315 should preferably be chosen such that liquid is prevented from passing through the edge barriers 325', 325".

The diaper in FIG. 3 is of the type which, during use, is fastened together in a pants shape around the lower part of the user's trunk. For this purpose, the diaper is provided with fastening members in the form of self-adhesive tapes 333, 334 which, before use, are folded in across the liquid-permeable cover sheet 302 of the diaper and fixed in a releasable manner to attachment surfaces 335, 336 with release characteristics.

The tapes 333, 334 are arranged on the side edges 309, 310 at the rear portion 307 of the diaper, near the end edge 312. When the diaper is being used, the tapes 333, 334 are folded out from the attachment surfaces 335, 336 so that the adhesive on the tapes 333, 334 is exposed. The tapes are then secured on a receiving area 337 arranged on the front portion 306 of the diaper. The receiving area 337 is situated on the outside of the liquid-tight cover sheet 303 and can simply constitute a part of this sheet. However, the liquid-tight cover sheet 303 is generally reinforced or otherwise treated in the receiving area in order to permit release and re-sealing of the tapes 333, 334 and/or in order to avoid the cover sheet 303 from being torn by the forces transmitted via the tapes.

To improve the fit and the attachment of the diaper to the shape of the user's body, elastic members 327, 328 are arranged along the front and rear end edges 311, 312, respectively. The elastic members 327, 328 are prestressed, for example between the cover sheets 302, 303 of the diaper, and form an elastic waist band during use. Suitable elastic members are bands, threads, etc., as has previously been described.

The liquid-permeable cover sheet 302 of the diaper 301 has a central zone 330, a front end zone 331 and a rear end zone 332. The material in the central zone 330 is more hydrophilic than the material in the end zones 331, 332.

Both the central zone 330 and the end zones 331, 332 extend along the entire width of the diaper, between the side edges 309, 310, and they thus form transverse zones across the surface of the diaper. Moreover, the central zone 330 is situated slightly nearer the front end edge 311 of the diaper than the rear end edge 312.

Figure 4:
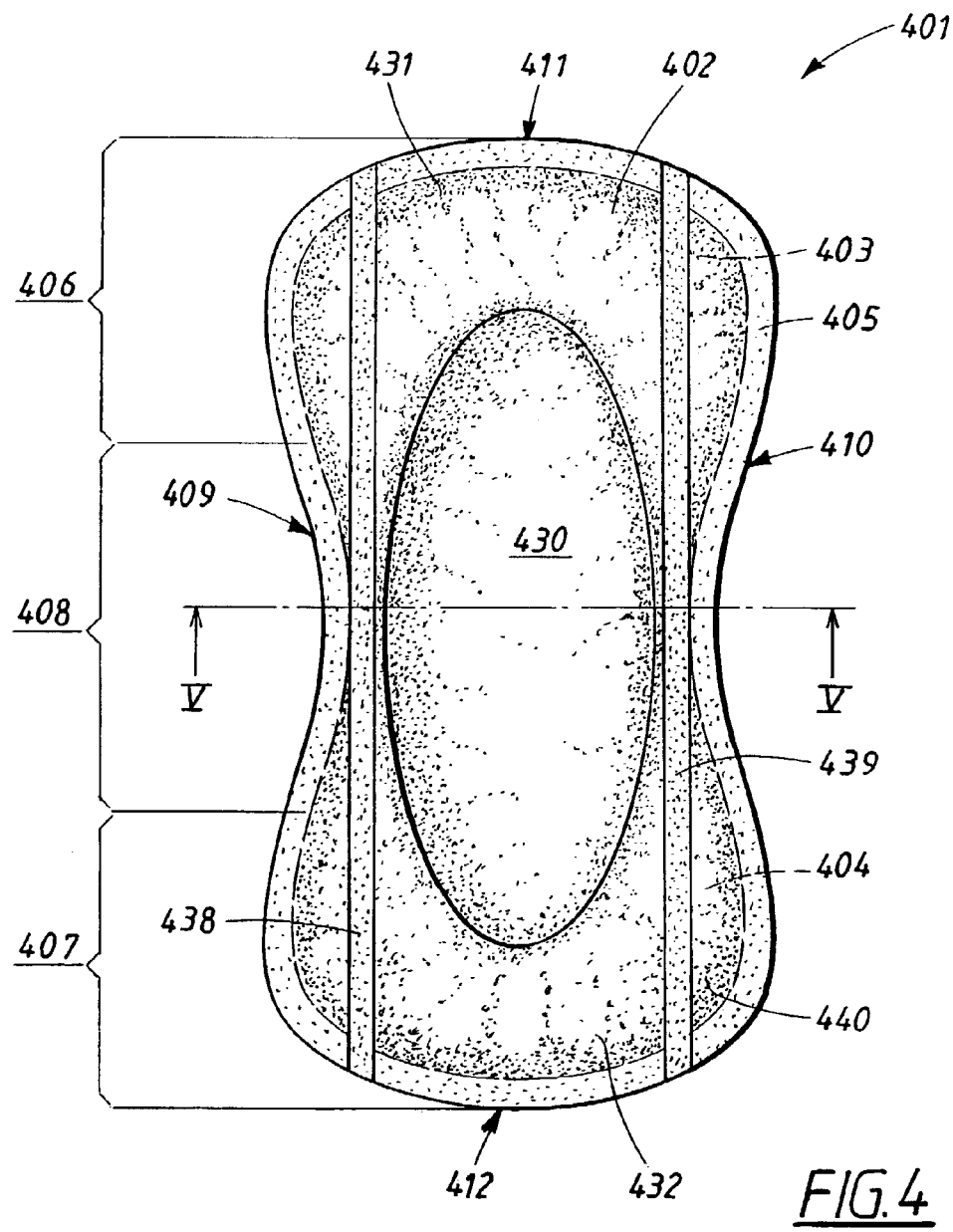
FIG. 4 shows a plan view of an incontinence protector according to a third embodiment of the invention.
Figure 5:
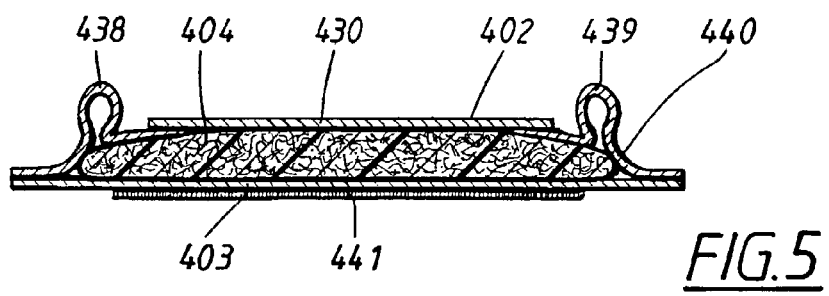
FIG. 5 shows a section along the line V-V through the incontinence protector in FIG. 4.

The incontinence protector 401 shown in FIGS. 4 and 5 also comprises a liquid-permeable cover sheet 402 and a liquid-tight cover sheet 403 which are connected to each other at an edge 405 around an absorbent body 404 arranged between the cover sheets 402, 403

The incontinence protector 401 is hourglass-shaped and has a narrower crotch portion 408 and wider end portions 406, 407. The incontinence protector also has longitudinal side edges 409, 410 and transverse end edges 411, 412.

Longitudinal folds in the liquid-permeable cover sheet 402 form raised edge barriers 425', 425". As has already been discussed in conjunction with the barrier layer 15 shown in FIGS. 1 and 2, it is advantageous for the material in the edge barriers 425', 425" to be sufficiently hydrophobic to prevent liquid penetration through the barriers 425', 425". Alternatively, the barriers can comprise further barrier sheets, for example of plastic film, or can be coated with liquid-tight material.

The liquid-permeable cover sheet 402 is made up of two different materials, of which a first material forms an oval central zone 403 which is more hydrophilic than the surrounding liquid-permeable cover sheet material which forms two end zones 431, 432. As can be seen from FIG. 4, the end zones 431, 432 constitute parts of a continuous material sheet 440 with an oval hole, to the edges of which the more hydrophilic material in the central zone 430 is attached. The parts included in the liquid-permeable cover sheet 402 can be joined together in any way suitable for the purpose, for example by adhesive bonding, or welding. FIG. 5 shows that the material in the central zone 430 is fixed to the outside of the more hydrophobic material sheet 440. Outside is here understood to mean that surface of the more hydrophobic material sheet 440 which is directed away from the absorbent body 404. However, it is alternatively possible to arrange the central zone 430 in such a way that it is fixed to the inside of the more hydrophobic material sheet 440.

By means of the fact that the more hydrophobic material sheet 440 is continuous along the side edges 409, 410 of the incontinence protector 401, the edge barriers 425', 425" can be formed as continuous folds in the more hydrophobic material sheet 440. It is of course advantageous for the edge barriers 425', 425" to be made of a relatively hydrophobic material, as in the material sheet 440, since this means that the barrier effect is thereby more pronounced than when the barriers 425', 425" have been made from the more hydrophilic material in the central zone 430.

The incontinence protector 401 is of the type which is secured inside the user's underwear, and it is for this purpose provided with a fastening means 441 in the form of a self-adhesive coating on the liquid-tight cover sheet 403.

Although only preferred embodiments are specifically illustrated and descried herein, it will be appreciated that many modifications and variations of the present invention are possible in light of the above teachings and within the purview of the appended claims without departing from the spirit and intended scope of the invention.

The invention claimed is:

1. An absorbent article for taking up body fluids, with a longitudinal direction, a transverse direction, a crotch portion and two end portions, and having side edges extending in the longitudinal direction and end edges extending in the transverse direction, and comprising a liquid-permeable cover sheet and a liquid-tight cover sheet, and an absorbent body arranged between the cover sheets, and further comprising barriers which are arranged along the side edges of the article and which are raised up from the liquid-permeable cover sheet, wherein the liquid-permeable cover sheet has a central zone arranged essentially in the crotch portion of the article, and two end zones arranged at the end portions of the article, the liquid-permeable cover sheet being more hydrophilic in the central zone than in the end zones and wherein the difference in hydrophilicity between the central zone and the end zones of the liquid-permeable cover sheet is obtained by the liquid-permeable cover sheet comprising an essentially hydrophobic material which has been treated to obtain hydrophilicity in the central zone, the central zone of the liquid-permeable cover sheet having an extent in the transverse direction of the article corresponding to 60-100% of a width of the article,
in which the central zone of the liquid-permeable cover sheet has an extent in the longitudinal direction of the article corresponding to 25-75% of a length of the article.

2. The absorbent article according to claim 1, wherein the raised edge barriers comprise elastic members.

3. The absorbent article according to claim 1, wherein the raised edge barriers comprise material which withstands liquid penetration.

4. The absorbent article according to claim 1, wherein the raised edge barriers are arranged along at least one end edge of the article.

5. The absorbent article according to claim 1, wherein the raised edge barriers are made of one and the same material layer and extend contiguously along the side edges and end edges of the article, as a result of which a pocket-like space is present between the edge barriers and the liquid-permeable cover sheet.

6. The absorbent article according to claim 1, wherein the central zone of the liquid-permeable cover sheet has been treated with wetting agent.

7. The absorbent article according to claim 1, wherein the central zone of the liquid-permeable cover sheet is centrally arranged in the longitudinal direction of the article.

8. The absorbent article according to claim 1, wherein the central zone of the liquid-permeable cover sheet is arranged slightly offset towards one end portion of the article.

9. The absorbent article according to claim 1, in which at least one elastic member is prestressed and in direct contact with the absorbent body, extending in an arcuate curve across the absorbent body, between the side edges of the article.

* * * * *

UNITED STATES PATENT AND TRADEMARK OFFICE
CERTIFICATE OF CORRECTION

PATENT NO. : 7,598,427 B2  Page 1 of 1
APPLICATION NO. : 10/203289
DATED : October 6, 2009
INVENTOR(S) : Ragnarson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1546 days.

Signed and Sealed this

Twenty-eighth Day of September, 2010

David J. Kappos
*Director of the United States Patent and Trademark Office*